(12) United States Patent
Yu

(10) Patent No.: US 11,578,413 B2
(45) Date of Patent: Feb. 14, 2023

(54) SABATIER REACTOR APPARATUS

(71) Applicant: Hamilton Sundstrand Corporation, Charlotte, NC (US)

(72) Inventor: Ping Yu, West Hartford, CT (US)

(73) Assignee: HAMILTON SUNDSTRAND CORPORATION, Charlotte, NC (US)

( * ) Notice: Subject to any disclaimer, the term of this patent is extended or adjusted under 35 U.S.C. 154(b) by 491 days.

(21) Appl. No.: 16/741,157

(22) Filed: Jan. 13, 2020

(65) Prior Publication Data
US 2021/0214848 A1 Jul. 15, 2021

(51) Int. Cl.
*C07C 1/12* (2006.01)
*C25B 1/04* (2021.01)
*B01D 53/04* (2006.01)
*C10L 3/08* (2006.01)

(52) U.S. Cl.
CPC .............. *C25B 1/04* (2013.01); *B01D 53/04* (2013.01); *B01D 53/0423* (2013.01); *C07C 1/12* (2013.01); *B01D 2253/102* (2013.01); *B01D 2253/304* (2013.01); *B01D 2253/308* (2013.01); *B01D 2257/306* (2013.01); *B01D 2259/4575* (2013.01); *C10L 3/08* (2013.01); *Y02E 60/36* (2013.01)

(58) Field of Classification Search
CPC ........ B01D 2253/102; B01D 2253/304; B01D 2253/308; B01D 2257/306; B01D 2259/4575; B01D 53/04; B01D 53/0423; C07C 1/12; C07C 9/04
See application file for complete search history.

(56) References Cited

U.S. PATENT DOCUMENTS

| | | | |
|---|---|---|---|
| 8,715,582 B1 | 5/2014 | Decker et al. | |
| 8,911,537 B2 | 12/2014 | Han et al. | |
| 9,186,472 B2 | 11/2015 | Cozean et al. | |
| 9,440,219 B2 | 9/2016 | Bohringer et al. | |
| 9,446,365 B2 | 9/2016 | Junaedi et al. | |
| 10,130,905 B2 | 11/2018 | Hoang et al. | |
| 2007/0028772 A1 | 2/2007 | Jain et al. | |
| 2012/0029095 A1* | 2/2012 | Junaedi | B01J 8/06 518/706 |

FOREIGN PATENT DOCUMENTS

WO 2009099395 A1 8/2009

* cited by examiner

*Primary Examiner* — Sharon Pregler
(74) *Attorney, Agent, or Firm* — Cantor Colburn LLP

(57) ABSTRACT

Disclosed is a Sabatier reactor apparatus including a carbon sorbent bed having an inlet for introducing a reactant stream to the carbon sorbent bed and an outlet for exiting a treated reactant stream from the carbon sorbent bed; and a Sabatier reactor having an inlet for introducing the treated reactant stream to the Sabatier reactor and an outlet for removing a product stream from the Sabatier reactor. Also disclosed is a method of preparing a reactant stream for a Sabatier reactor.

16 Claims, 1 Drawing Sheet

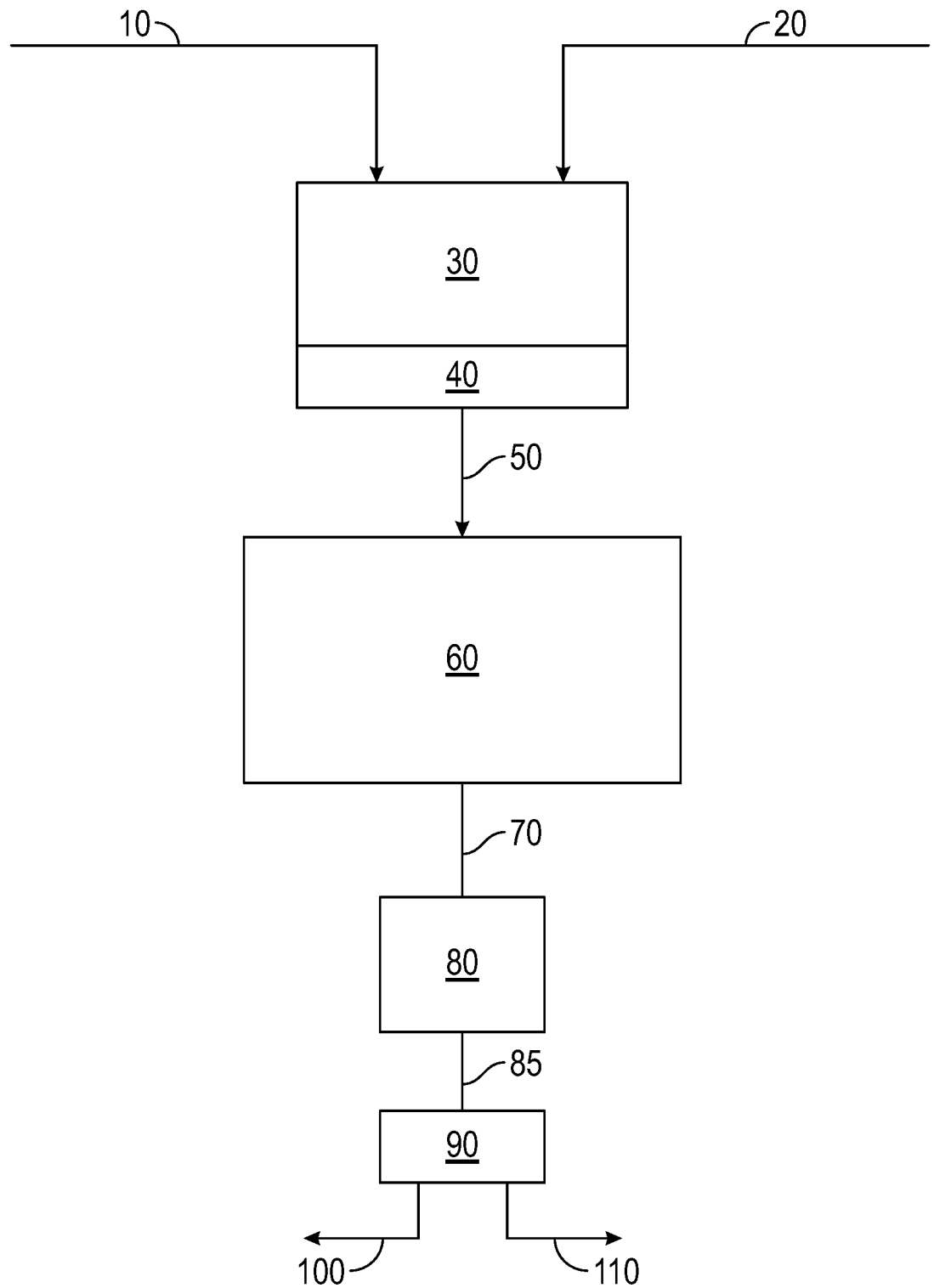

SABATIER REACTOR APPARATUS

BACKGROUND

The Sabatier reaction provides a method for in-situ resource utilization of carbon dioxide and for production of required human consumables, specifically, water and oxygen, for space missions. The Sabatier reaction specifically converts a mixture of carbon dioxide and hydrogen in the presence of a catalyst into a mixture of water and methane. The reaction accomplishes a primary goal of converting carbon dioxide, built-up in a space capsule or ubiquitous to an extraterrestrial environment, into valuable human consumables, specifically water, which is valued in itself or is converted into life-supporting oxygen. The Sabatier reaction eliminates the need to transport large quantities of water from Earth into space and, in this aspect, the Sabatier reaction reduces the payload projected from Earth and maintained on space voyages.

Improvements to the Sabatier system are desired to improve system productivity and longevity.

BRIEF DESCRIPTION

Disclosed is a Sabatier reactor apparatus including a carbon sorbent bed having an inlet for introducing a reactant stream to the carbon sorbent bed and an outlet for exiting a treated reactant stream from the carbon sorbent bed; and a Sabatier reactor having an inlet for introducing the treated reactant stream to the Sabatier reactor and an outlet for removing a product stream from the Sabatier reactor.

In addition to one or more of the features described above, or as an alternative to any of the foregoing embodiments, the carbon sorbent bed includes activated carbon.

In addition to one or more of the features described above, or as an alternative to any of the foregoing embodiments, the activated carbon has a pore size greater than or equal to 1 nanometer (nm).

In addition to one or more of the features described above, or as an alternative to any of the foregoing embodiments, the activated carbon has a particle size of 4 mesh to 40 mesh.

In addition to one or more of the features described above, or as an alternative to any of the foregoing embodiments, the reactant stream comprises dimethyl sulfone and the treated reactant stream comprises less than or equal to 0.1 mg/m$^3$ of the dimethyl sulfone in the reactant stream.

In addition to one or more of the features described above, or as an alternative to any of the foregoing embodiments, the carbon sorbent bed is located in a housing with the Sabatier reactor.

In addition to one or more of the features described above, or as an alternative to any of the foregoing embodiments, the carbon sorbent bed is located in a separate housing from the Sabatier reactor.

In addition to one or more of the features described above, or as an alternative to any of the foregoing embodiments, the Sabatier reactor apparatus further includes a filtration device.

In addition to one or more of the features described above, or as an alternative to any of the foregoing embodiments, the filtration device is combined with the carbon sorbent bed.

Also disclosed is a method of preparing a reactant stream for a Sabatier reactor including contacting the reactant stream with a carbon sorbent to form a treated reactant stream and introducing the treated reactant stream to a Sabatier reactor.

In addition to one or more of the features described above, or as an alternative to any of the foregoing embodiments, the reactant stream includes hydrogen, carbon dioxide or a combination thereof.

In addition to one or more of the features described above, or as an alternative to any of the foregoing embodiments, the reactant stream comprises dimethyl sulfone and the treated reactant stream comprises less than or equal to 0.1 mg/m$^3$ of the dimethyl sulfone in the reactant stream.

In addition to one or more of the features described above, or as an alternative to any of the foregoing embodiments, the carbon sorbent bed includes activated carbon.

In addition to one or more of the features described above, or as an alternative to any of the foregoing embodiments, the activated carbon has a pore size greater than or equal to 1 nm.

In addition to one or more of the features described above, or as an alternative to any of the foregoing embodiments, the activated carbon has a particle size of 4 mesh to 40 mesh.

In addition to one or more of the features described above, or as an alternative to any of the foregoing embodiments, the reactant stream comprises a contaminant selected from the group consisting of dimethyl sulfone, a siloxane, an organic fluorine compound, an organic compounds containing chlorine or a combination thereof and the treated reactant stream comprises less of the contaminant than the reactant stream.

BRIEF DESCRIPTION OF THE DRAWINGS

The following descriptions should not be considered limiting in any way.

The FIGURE is a schematic of a Sabatier apparatus.

DETAILED DESCRIPTION

A detailed description of one or more embodiments of the disclosed apparatus and method are presented herein by way of exemplification and not limitation with reference to the FIGURE.

Carbon dioxide and hydrogen may be reacted in a Sabatier reactor to produce methane and water. Electrolysis can produce oxygen and hydrogen from water. The combination of the Sabatier reaction and electrolysis converts carbon dioxide to oxygen, hydrogen and methane. Thus carbon dioxide, built up as the result of respiration in an enclosed environment, can be used to produce human consumables such as oxygen and water.

The Sabatier reaction relies on catalysis. Exemplary catalysts include iron, cobalt, nickel, ruthenium, rhodium, palladium, osmium, iridium, platinum, or a combination thereof, more specifically nickel, ruthenium, rhodium, or a combination thereof. The catalyst may be supported by an oxide support in any form such as a mesh, a tube, a particle bed or a combination thereof. The activity of the catalyst may be reduced by exposure to one or more contaminants. Exemplary contaminants include dimethyl sulfone (DMSO$_2$), siloxanes such as polydimethyl siloxane, organic fluorine compounds such as R-134a, and organic compounds containing chlorine such as dimethyl chloride. These contaminants may be present in very low amounts in the reactant stream to the Sabatier reactor. However they can accumulate over time in amounts sufficient to lower the activity of the catalyst and reduce the effectiveness and efficiency of the Sabatier reactor. For example, dimethyl sulfone is a solid at room temperature (23° C.) and would not be expected to be found as a contaminant in a reactant stream of gaseous components such as carbon dioxide and hydrogen. Nonetheless dimethyl sulfone has been shown to be a primary contaminant in failed Sabatier reactors and removal of dimethyl sulfone to very low levels is desired.

Introducing the reactant stream to a carbon sorbent to produce a treated reactant stream and then introducing the treated reactant stream to the Sabatier reactor is an effective and efficient method to reduce the dimethyl sulfone concentration as well as the concentration of other contaminants in the treated reactant stream and prolong the life of the Sabatier reactor catalyst. The treated reactant stream may have a dimethyl sulfone concentration of less than or equal to 0.1 milligrams per cubic meter ($mg/m^3$). The reactant stream and the treated reactant stream may comprise hydrogen, carbon dioxide or both. More explicitly there may be two reactant streams, a hydrogen stream and a carbon dioxide stream and each may be introduced to a separate carbon sorbent or the two streams may enter a common carbon sorbent. It is also contemplated that the reactant stream entering the carbon sorbent may include both carbon dioxide and hydrogen. It is further contemplated that only one of a hydrogen stream or a carbon dioxide stream may be introduced to the carbon sorbent.

The treated reactant stream may, individually or in combination, have a contaminant concentration as shown in Table 1.

TABLE 1

| Contaminant | Concentration |
| --- | --- |
| Siloxane | Less than or equal to 5 $mg/m^3$ |
| R-134a | Less than or equal to 1 $mg/m^3$ |
| Dimethyl chloride | Less than or equal to 0.1 $mg/m^3$ |

The carbon sorbent includes activated carbon. Activation of carbon is the process of treating the carbon to open a large number of pores in the 1 to 20 nanometer diameter range or up to 100 nanometer diameter range. Almost any carbonaceous raw material can be used for the manufacture of activated carbon. Nut shells (particularly coconut), coal, petroleum coke and other residues in either granular, briqueted or pelleted form are illustrative examples of materials which can be used. After activation the carbon has the large surface area (for example 500-1500 square meters/gram) responsible for adsorption. The activation process may include thermal decomposition in a furnace using a controlled atmosphere and heat. Exemplary activated carbons include NORIT® ROZ 3 available from Cabot Corporation.

The activated carbon may have a pore diameter greater than or equal to 1 nanometer (nm) or greater than or equal to 100 nm. The activated carbon may have a particle size of 4 mesh size to 40 mesh size (US mesh).

In some embodiments the carbon sorbent removes greater than or equal to 99 weight % of the dimethyl sulfone found in the reactant stream.

The design of the Sabatier reactor is not particularly limited and may be any of those known in the art. In some embodiments there may also a filtration device for the reactant stream or treated reactant stream prior to entry to the reactor. In some embodiments the carbon sorbent bed may be combined with the filtration device.

It is further contemplated that the carbon sorbent may be located within the same housing the Sabatier reactor. In some embodiments, regardless of location, the carbon sorbent is a modular element that may be replaced at desired times to prevent contamination of the reactant stream. The replacement may be performed on a scheduled maintenance basis (i.e., at scheduled intervals) or may be performed in response to detection of unacceptable levels of one or more contaminants.

An exemplary apparatus is shown in the FIGURE. Two reactant streams 10 and 20 enter the carbon sorbent 30 which is immediately followed by a filtration bed 40. A treated reactant stream 50 exits the filtration bed and enters the Sabatier reactor 60. The product stream 70 exits the Sabatier reactor 60 and enters a condensing heat exchanger 80. The condensed product stream 85 exits the condensing heat exchanger 80 and enters the gas separator 90. Two separated condensed product streams 100 and 110 leave the gas separator.

The term "about" is intended to include the degree of error associated with measurement of the particular quantity based upon the equipment available at the time of filing the application.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A Sabatier reactor apparatus comprising:
   a carbon sorbent bed having an inlet for introducing a reactant stream to the carbon sorbent bed and an outlet for exiting a treated reactant stream from the carbon sorbent bed, wherein the carbon sorbent bed removes dimethyl sulfone from the reactant stream to produce the treated reactant stream; and
   a Sabatier reactor having an inlet for introducing the treated reactant stream to the Sabatier reactor and an outlet for removing a product stream from the Sabatier reactor.

2. The Sabatier reactor apparatus of claim 1, wherein the carbon sorbent bed comprises activated carbon.

3. The Sabatier reactor apparatus of claim 2, wherein the activated carbon has a pore size greater than or equal to 1 nm.

4. The Sabatier reactor apparatus of claim 2, wherein the activated carbon has a particle size of 4 mesh to 40 mesh.

5. The Sabatier reactor apparatus of claim 1, wherein treated reactant stream comprises less than or equal to 0.1 $mg/m^3$ of the dimethyl sulfone in the reactant stream.

6. The Sabatier reactor apparatus of claim 1, wherein the carbon sorbent bed is located in a housing with the Sabatier reactor.

7. The Sabatier reactor apparatus of claim 1, wherein the carbon sorbent bed is located in a separate housing from the Sabatier reactor.

8. The Sabatier reactor apparatus of claim 1, further comprising a filtration device.

9. The Sabatier reactor apparatus of claim 8, wherein the filtration device is combined with the carbon sorbent bed.

10. A method of preparing a reactant stream for a Sabatier reactor comprising:
    contacting the reactant stream with a carbon sorbent to form a treated reactant stream such that the carbon sorbent removes dimethyl sulfone from the reactant stream to form the treated reactant stream; and
    introducing the treated reactant stream to the Sabatier reactor.

11. The method of claim 10, wherein the reactant stream comprises hydrogen, carbon dioxide or a combination thereof.

12. The method of claim 10, wherein the the treated reactant stream comprises less than or equal to 0.1 mg/m$^3$ of the dimethyl sulfone in the reactant stream.

13. The method of claim 10, wherein the carbon sorbent bed comprises activated carbon.

14. The method of claim 13, wherein the activated carbon has a pore size greater than or equal to 1 nm.

15. The method of claim 13, wherein the activated carbon has a particle size of 4 mesh to 40 mesh.

16. The method of claim 10, wherein the reactant stream comprises a contaminant selected from the group consisting of dimethyl sulfone, a siloxane, an organic fluorine compound, an organic compounds containing chlorine or a combination thereof and the treated reactant stream comprises less of the contaminant than the reactant stream.

* * * * *